US006396069B1

(12) United States Patent
MacPherson et al.

(10) Patent No.: US 6,396,069 B1
(45) Date of Patent: May 28, 2002

(54) TOPOGRAPHER FOR REAL TIME ABLATION FEEDBACK HAVING SYNTHETIC WAVELENGTH GENERATORS

(76) Inventors: David C. MacPherson, 11579 Apache Trail, Conifer, CO (US) 80433; Jon G. Dishler, 6295 S. Macon Way, Englewood, CO (US) 80111

( * ) Notice: Subject to any disclaimer, the term of this patent is extended or adjusted under 35 U.S.C. 154(b) by 0 days.

(21) Appl. No.: 09/344,339

(22) Filed: Jun. 25, 1999

(51) Int. Cl.$^7$ ............................................... G01N 21/86
(52) U.S. Cl. ................... 250/559.22; 350/216; 356/376
(58) Field of Search ....................... 250/559.22, 559.21, 250/559.4, 559.39, 216; 356/376, 379, 349, 345, 357

(56) References Cited

U.S. PATENT DOCUMENTS

| 4,387,994 A | 6/1983 | Balasubramanian |
| 5,153,669 A | * 10/1992 | DeGroot ..................... 356/349 |
| 5,307,097 A | 4/1994 | Baker |
| 5,317,389 A | 5/1994 | Hochberg et al. |
| 5,350,374 A | 9/1994 | Smith |

FOREIGN PATENT DOCUMENTS

| EP | 0 401 799 A2 | 12/1990 |
| EP | 0 506 297 A2 | 9/1992 |
| WO | WO 98/08048 | 2/1998 |
| WO | WO 99/01716 | 1/1999 |

OTHER PUBLICATIONS

R. Dandliker, T. Thalmann, and D. Prongue, "Two–Wavelength Laser Interferometry Using Superheterodyne Detection," Optics Letters, vol. 13, No. 5, May 1988.

E. Gelmeni, U. Minoni, and F. Docchio, "Tunable, Double–Wavelength Heterodyne Detection Interferometer for Absolute–Distance Measurenments," Optics Letters, vol. 19, No. 3, Feb 1, 1994.

Z. Sodnik, E. Fischer, T. Ittner, and H.J. Tiziani, Two–Wavelength Double Heterodyne Interferometry Using a Matched Grating Technique, Aug. 1991.

* cited by examiner

Primary Examiner—Que T. Le

(57) ABSTRACT

A surface contouring system may be provided with a topographer to measure the surface contours. The topographer may be a laser topographer that measures the surface contours using superheterodyne synthetic wavelength interferometry. The maximum vertical step size dictated by the limits of conventional laser interferometry may be increased by creating laser signals with synthetically-generated longer effective wavelengths. The topographer may perform sequential scans rapidly so that measurement feedback can be used to interactively control the shape of the surface being measured. The interferometer may use counter-rotating optical wedges to create a rotating, radially looping scan pattern that concentrates measurement density in the center portions of the target surface. Different embodiments of the topographer may be applied to diverse uses such as corneal ablation procedures, precision machining operations, and vibration analysis.

38 Claims, 8 Drawing Sheets

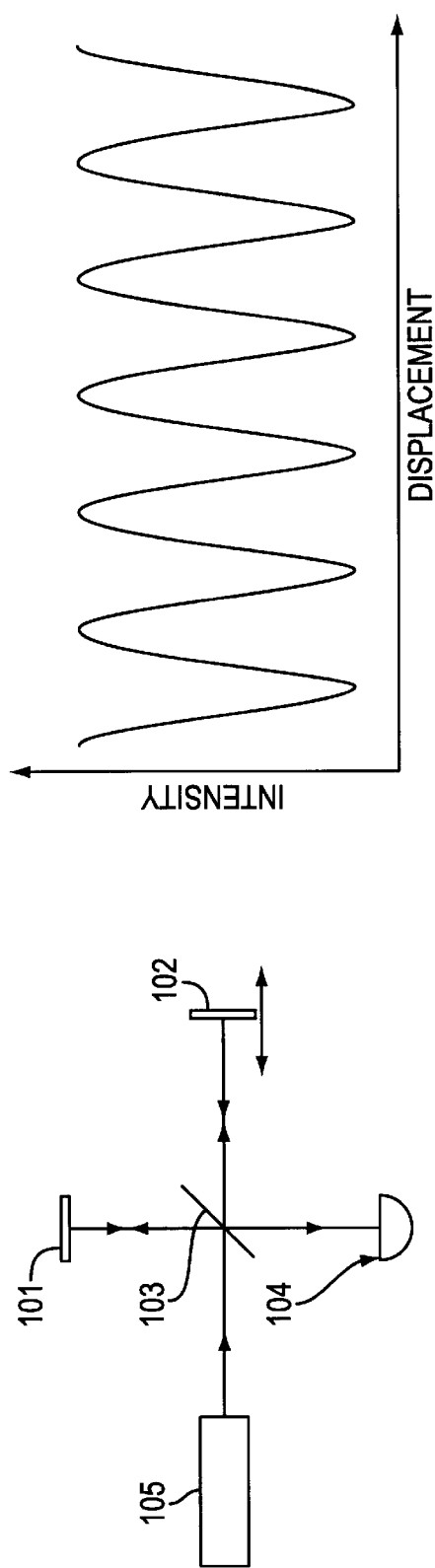
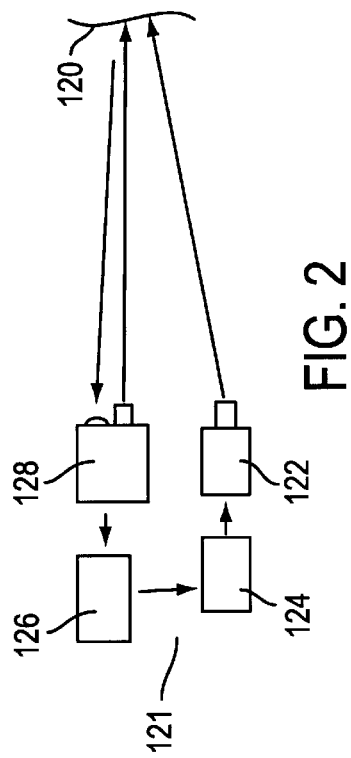
FIG. 1A (PRIOR ART)
FIG. 1B (PRIOR ART)
FIG. 2

TOPOGRAPHER FOR REAL TIME ABLATION FEEDBACK HAVING SYNTHETIC WAVELENGTH GENERATORS

This invention was made with government support under SBIR grant number 1 R43 EY12322-01 awarded by the National Institute of Health. The government has certain rights in the invention.

BACKGROUND OF THE INVENTION

1. Field of the Invention

The invention relates to an interferometer system that can be used to measure surface topography and surface movement with extreme accuracy and with sufficient rapidity to provide real-time feedback of changes in the topography or movement of the surface. In particular, the invention relates to an apparatus and method for using laser interferometry to obtain real-time feedback on: 1) the shape of a cornea as the cornea is being reshaped through a vision-correction process referred to as corneal photo-ablation, 2) the shape of precision manufactured components during manufacture, 3) non-contact measurement of vibration, and 4) movement in a rotating object.

2. Description of the Related Technology

In recent years laser interferometer devices have been developed for measuring a change in distance with extreme accuracy. Such devices generally direct a narrow laser beam onto a spot on a surface, detect the returned radiation, and use interferometry techniques to determine a change in distance along the optical axis of the laser beam. Such devices, however, typically only monitor the one spot, and do not measure the broader topography of the surface. As a result, things such as surface contours, rotational movement, and movement along any axis other than that of the laser beam are not detected.

Other devices, called topographers, have been developed for measuring surface contours. These are usually designed to map a stationary surface, so speed of operation is not critical. Topographers generally map the contours of a surface by determining the relative elevation of different points on that surface, and assuming a relatively constant slope between those two points. Elevation is defined by the distance from the point being measured to the measurement device, as measured along the axis of the returning signal. Since it is the change in elevation from one point to the next that defines the surface contour, it is generally only necessary to determine the relative change in elevation from point to point rather than the absolute elevation of any given point.

Topographers usually operate by directing a signal of some kind to a point on the surface to be mapped, detecting the signal bounced back from that point, and repeating the process for various other points. Points at different elevations will return different signals. By comparing the difference in signals returned from different points, the difference in elevation between those points can be determined. With enough data points, the contour of the entire surface can be mapped.

To measure the contours of a surface with microscopic accuracy, a topographer should be able to determine the relative elevation of a large number of individual points on that surface with extreme precision. Laser interferometers are known for their ability to make precise measurements of a change in elevation of a single point. A simple Michelson interferometer can be used to illustrate the basic technique as shown in FIG. 1a. The output from a laser 105 is divided into two beams by beam splitter 103. The first of the resulting beams is reflected back to beam splitter 103 by mirror 101, which is fixed and thus produces a fixed optical path length. The second beam is reflected back to beam splitter 103 by mirror 102, which can be moved along the optical axis as shown by the arrow. This movement changes the optical path length of the second beam by twice the amount of movement. Portions of these two reflected beams are combined at beam splitter 105 and this combined beam is sent to a detector 104. As mirror 102 is moved along the optical axis, the intensity at the detector varies as shown in FIG. 1b, due to the manner in which the phases of the two return beams combine. A mirror movement of one half the laser wavelength causes one full oscillation cycle in the measured intensity. Mirror movement is determined by counting the number of intensity oscillations, or 'fringes'. Hence, physical movements can be accurately detected with this method within a fraction of one-half wavelength by examining the phase position within a fringe cycle. Since the wavelength of laser radiation is typically on the order of a micron, changes of a fraction of a micron can be accurately measured in this manner. However, this technique is effective only if the vertical step size (the change in elevation between successive measurements) is less than one-half wavelength. Since the fringe counter is based on phase differences, multiples of one-half wavelength cannot be detected and only the residual fraction of one-half wavelength will be measured.

Using a Michelson interferometer is an accurate method of measuring a change in elevation of a given point, as that elevation changes with time. Unfortunately, it requires the mirror (or other optically smooth surface) to be perpendicular to the beam, or the reflected light will miss the sensor. However, the same basic principles can be used for detecting laser light that is scattered from an optically rough surface. Optically rough surfaces scatter light by returning it in many different directions at once. However, by using a small-diameter laser beam and a small detector, only the light scattered along a narrow, predictable return path will be detected, thereby simulating parallel reflected light. Although the returned light might be much weaker than with a reflected signal, this is offset by the benefits of detecting light from spots that are not perpendicular to the laser beam.

The fixed mirror of the Michelson interferometer can be replaced with a flat but optically-rough reference surface, while the moveable mirror can be replaced with an optically-rough non-flat target surface to be measured. Instead of moving the target surface along the optical axis, the small-diameter laser beam can be scanned across the target surface, causing changes in elevation on the surface to produce the same fringe effects previously noted. By controlling the scan pattern so that each fringe measurement corresponds to a known location on the target, the surface contours of that target can be accurately mapped. However, this technique has the same limitations noted above. If the vertical step size, or change in elevation between sequentially measured spots, is greater than one-half wavelength, the fringe counter will only detect the residual fraction of half a wavelength. Similar confusion results if an individual spot being measured contains variations in elevation larger than one half wavelength.

This is one of the major drawbacks of laser-based topographers. Most lasers that are suitable for this application operate with wavelengths in the micron and submicron range. Thus any change in elevation between two sequentially-measured points must be much less than a micron or it won't be accurately measured. For most applications, this requires that the two adjacent points be very close together, to avoid the cumulative effects of moving up or down a sloping surface. However, this closeness increases the number of points that must be measured for a given surface area. Using a standard rectangular grid of measurement points, as the spacing between measurement points decreases by a given proportion, the amount of measuring and processing will increase as the square of that proportion. Thus the processing becomes unwieldy and slow, and the time it takes to do a single surface scan increases accordingly. For mapping the surface of a small stationary object, this may not be objectionable. But mapping the surface of an object with a changing surface requires completing sequential scans in real time so the changes in that surface with time can be determined. In these cases, the short wavelength of the laser beam can be a detriment because it requires more closely spaced measurement points, which increases the time to complete each scan. The operator must sacrifice speed for accuracy, or vice-versa.

To solve these problems, the laser radiation needs to have a wavelength which is at least twice as large as the maximum surface roughness (elevation variation) expected to be encountered between reasonably-spaced measurements points. Unfortunately, lasers which are suitable for this application all have comparatively short wavelengths. Long wavelength lasers exist, but it is not possible to focus a long wavelength laser to a small enough spot for most applications. Many potential applications for laser interferometer topography cannot use conventional laser topographers because the expected surface variation of the target is too great.

To overcome all the problems noted above, a device and process is needed that uses an interferometer that can measure surface contours over a variety of roughness ranges that provides this measurement data quickly enough to rapidly make successive scans, and that measures enough points to minimize the likelihood that undetected irregularities between measured points will unacceptably degrade the results. To use the techniques of laser interferometry in this application, a light source is needed that provides a monochromatic beam with the wavelength stability of laser light, but with a wavelength longer than that permitted by the requirement to focus the laser to a small spot. This wavelength should preferably also be adjustable to accommodate different roughness ranges without requiring a major system redesign.

SUMMARY OF THE INVENTION

The present invention addresses the aforementioned problems in the prior art through a unique combination of laser interferometry, optical superheterodyning, and synthetic wavelength generation. This process is referred to as "superheterodyne synthetic wavelength interferometry". A system implementing this process can include a scattered-light interferometer, a superheterodyne optical system for generating and using synthetic wavelength beams, an interferometer control system that controls the interferometer for surface topography measurements, a feedback control system, and a target control system for manipulating or modifying the target surface. Most of these components may be similar in all applications. However, the target control system may vary greatly, depending on the application. For instance, a medical system for reshaping the cornea of a human patient is much different that a system for manufacturing precision metal components.

The laser source may be any wavelength-stabilized laser, but preferred lasers may include such types as distributed feedback diode lasers (DBF), distributed Brag reflector diode lasers (DBR), extended cavity diode lasers, or diode pumped solid state lasers. These are all well-known laser types that are commercially available. Eye-safe lasers, such as those with a wavelength near 1550 nm are preferred for safety reasons. To make the topographer's laser radiation suitable for particular applications, optical superheterodyne techniques may be used to synthetically increase the laser's effective wavelength until it is long enough to detect the anticipated elevation changes and surface irregularities.

The invention may use four optical frequencies: f1, f2, f3 (which may be a frequency-shifted f1), and f4 (which may be a frequency-shifted f2). Unlike conventional devices, which send f1+f2 to the target surface and f3+f4 to the reference surface, the invention may send f1+f2 to both the target and reference surfaces, and mix their returned signals with a local oscillator signal f3+f4.

The interferometer may measure optically-rough target surfaces and use an optically-rough reference surface, thus eliminating the need for either the target surface or the reference surface to be precisely perpendicular to the laser beams.

The interferometer may use counter-rotating, wedges to generate the scan pattern.

The interferometer may operate with two synthetic wavelength beams having, different synthetic wavelengths, with the difference between the two synthetic wavelengths being much smaller than either synthetic wavelength. The first synthetic wavelength may be formed by using a first polarizing beam splitter to combine a p-polarized portion of a first laser beam with an s-polarized portion of a second laser beam. The linear polarized components may be converted to left and right circular polarized components using a first quarter wave plate. After passing through a non-polarizing beam splitter, focus control, and scanning mechanism, this mixture of optical signals may be directed to both the target surface and the reference surface with a second polarizing beam splitter. The portions of these signals which are scattered back from the two surfaces can be directed back along the same path to the non-polarizing beam splitter.

The second synthetic wavelength may be formed by using a third polarizing beam splitter to combine an s-polarized frequency-shifted portion of the first laser beam with a p-polarized frequency-shifted portion of the second laser beam. The frequency shifts can be accomplished with first and second acousto-optic modulators operating at different frequencies. The resulting linear polarized components may be converted to left and right circular polarized components using a second quarter wave plate. After passing through the non-polarizing beam splitter, the left and right circularized components may be mixed to form the second synthetic wavelength.

The second synthetic wavelength and the returned components of the first synthetic wavelength may be combined in the non-polarizing beam splitter and passed through a third polarizing beam splitter where they may be separately directed to a target surface signal sensor and a reference surface signal sensor. The outputs of the two sensors may then be analyzed to detect fringe patterns.

One embodiment of the invention can be used in a system to ablate corneal tissue, by using the interferometer system to map the topography of the surface of an ablated cornea, determining the difference between the surface contour and an expected contour, changing the ablation parameters based on this difference, and continuing the ablation based on the changed parameters.

Another embodiment of the invention can be used in a system to manufacture precision machine parts by using the interferometer system to map the topography of the surface of a part during machining, determining the difference between the surface contour and an expected contour, changing the machining parameters based on this difference, and continuing the machining operation based on the changed parameters.

Another embodiment of the invention can be used in a system to measure surface vibrations by using the interferometer system to measure the topography of multiple points on the test object, repeating the measurements at short time intervals, and using the difference in elevation between successive measurements for each point to analyze the vibration characteristics of that point. The invention can also be used to measure the transverse motion of a rotating point (i.e., a point on a rotating wheel) by scanning the laser beam in a circular pattern, and synchronizing the rotational speed of the scan with the rotational speed of the target so that the laser beam continues to impinge on a single point of the rotating target.

It is an object of the invention to provide a topographer to accurately measure the contours of a surface.

It is a further object of the invention to measure elevation changes in the surface to an accuracy of less than two microns.

It is a further object of the invention to provide data on these measurements quickly enough and often enough to interactively control a process of modifying the surface.

It is a further object of the invention to measure enough points on the surface to detect correctable irregularities on that surface.

It is a further object of the invention to measure the shape of a surface being changed by radiation, such as a cornea during an ablation process, and use the measured shape to interactively control the ablation process.

It is a further object of the invention to measure the shape of a mechanical part being changed by mechanical means, such as a machined part during a machining operation, and use the measured shape to interactively control the mechanical means.

It is a further object of the invention to measure the vibration characteristics of multiple points on a vibrating object, without physically contacting the object with measurement devices.

It is a further object of the invention to measure the motion of at least one point on a rotating surface in a direction parallel to the axis.

BRIEF DESCRIPTION OF THE DRAWINGS

FIGS. 1a and 1b show a Michelson interferometer of the prior art.

FIG. 2 shows a simplified overview of a complete system containing the topographer of the invention.

DETAILED DESCRIPTION OF THE INVENTION

Figure 3:
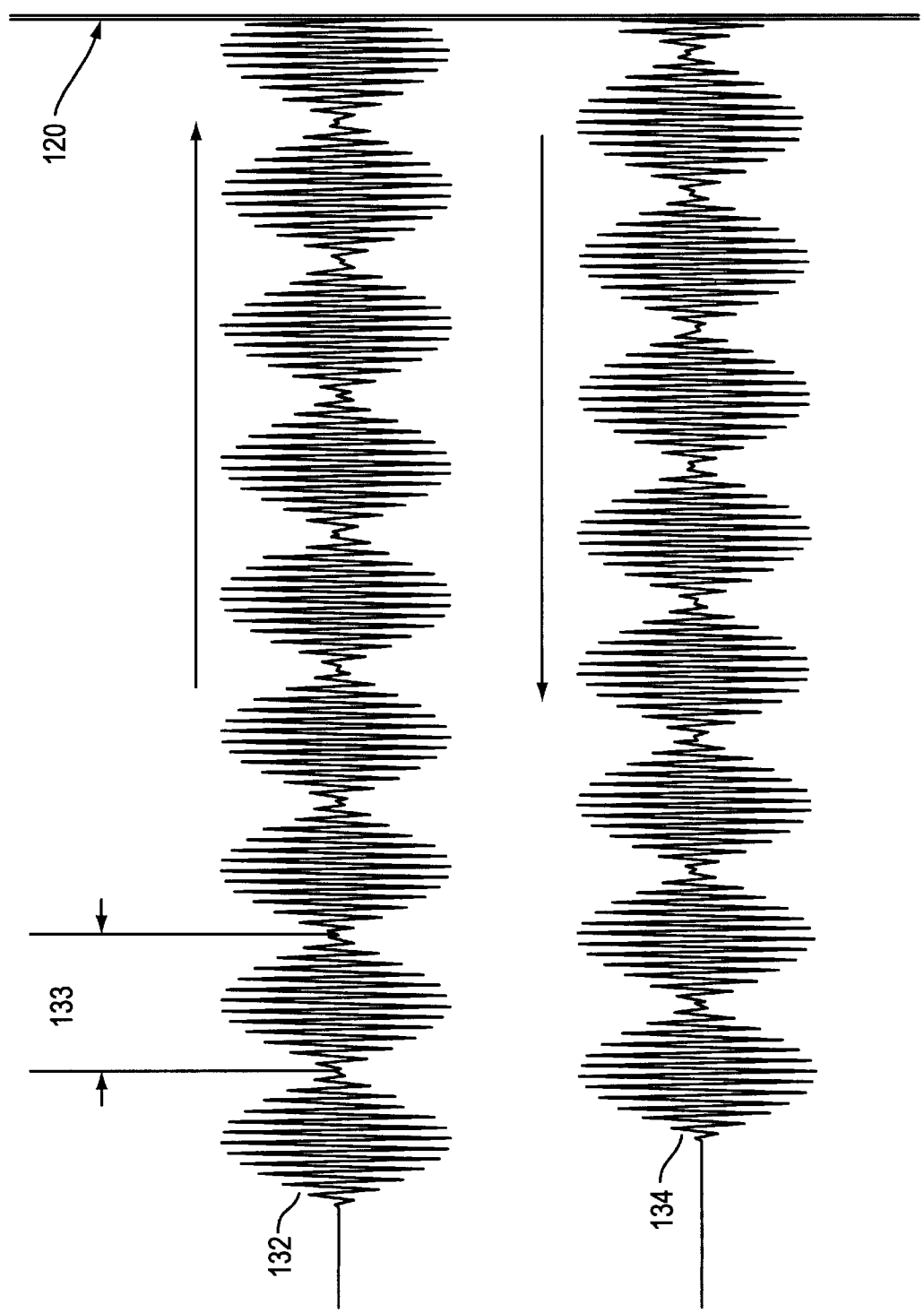
FIG. 3 shows the beat pattern formed by combining two laser beams of different wavelength.

FIG. 2 shows a block diagram of a generic system using the invention. Modification device 122 can operate in some manner on target surface 120. This might include, but is not limited to, an excimer laser ablating surface tissue from a patient's cornea, a machine tool modifying the shape of a manufactured part, or a vibration machine inducing vibrations in surface 120. These three applications are described later in greater detail, but many other applications can also benefit from the invention. The specific operations being performed on surface 120 may be controlled by device controller 124. Topographer 128 may direct laser radiation onto surface 120. A portion of that radiation may be scattered back to a sensor in topographer 128, where the sensor data may be interpreted by feedback controller 126. Feedback controller 126 can then compare the interpreted data with a database of expected results, and derive correction factors for device controller 124. These correction factors can then be used to alter the database which defines the operation of modification device 122. Through this method of repetitive feedback, intermediate results that differ from the expected results can be corrected during the modification process. The functions of control, measurement, and feedback are preferably aided by computers, though hard-wired circuits may also be used. Although described as being in separate controllers, these functions may be combined as needed into multi-purpose controllers, with common computers or circuitry performing multiple functions. The supporting hardware may also be combined or separated as needed. These design decisions are well within the abilities of average circuit design engineers.

Laser Interferometer

As previously stated, the characteristics of laser interferometry make it ideal for measuring sub-micron elevation changes on a surface, but the wavelength of a typical laser is too short to detect surface irregularities and elevation changes that are significantly larger than that. Unfortunately, lasers with the desired longer wavelengths cannot be used because their beams cannot be focused to a sufficiently small spot. However, laser radiation with a longer effective wavelength can be generated synthetically.

FIG. 3 shows a synthetic wave which is formed by adding two laser beams with different wavelengths. Due to the changing phase differences between the two, in which they alternately reinforce or cancel each other, the combined waves generate "beat" pattern 132. Beat pattern 132 contains both a higher frequency component with a short wavelength and a lower frequency component with a synthetic "beat" wavelength 133. Beat pattern 132 can be returned from surface 120 as returned beat pattern 134. In normal operation, the signals forming patterns 132 and 134 would travel along the same axis in opposite directions, and would thus overlap each other. They are shown separated in FIG. 3 only for conceptual clarity, so that the characteristics of each are more plainly visible.

As previously described, the laser radiation can be reflected from an optically smooth surface, but in a preferred embodiment it is scattered from an optically rough surface 120, meaning that the return signal is scattered in many different directions. But by using a small detector, only that part of the signal returning in a narrow, essentially parallel direction is detected. Thus a scattered light interferometer can produce the same results as a reflected light interferometer, although the intensity of the detected return signal is much less for a scattered light system. Beat pattern 134 might have an amplitude much less than beat pattern 132, and the conceptual illustrations of FIG. 3 do not indicate relative signal amplitudes.

If an interferometer is made that counts beats instead of fringes then synthetic wavelength 133 can determine the accuracy and precision of the associated topographer. The beat counter will not be confused as long as the surface being measured does not have roughness or elevation changes larger than one half of synthetic wavelength 133. Synthetic wavelength 133 depends on the difference in wavelengths of the two laser beams being combined to form beat pattern 132—the smaller this difference, the longer the synthetic wavelength 133. Thus by carefully selecting the wavelengths of the two lasers, a synthetic wave with the desired effective wavelength can be created. Tunable diode lasers are ideal for this process, since their individual wavelengths can be adjusted to produce a beat pattern with the desired effective wavelength. This also permits the topographer to be adjusted to measure different ranges of elevation change.

In a preferred embodiment, the topographer uses a synthetic wavelength of 400 microns. As long as surface 120 does not have abrupt elevation changes greater than 200 microns, the beat counter can keep track of successive elevation changes during a scan. In addition, the spot on surface 120 illuminated by the laser must not encompass elevation differences greater than 200 microns. The frequency difference for the two lasers in this embodiment is 754 GHz. With this configuration, the beat counter must have an accuracy of $\frac{1}{200}^{th}$ of a beat in order to achieve 1 micron accuracy. This high accuracy should also be obtained in a short time to permit the laser beam to rapidly scan across surface 120. Making a fast accurate measurement requires a good signal to noise ratio, which can be obtained using heterodyne detection.

Heterodyne Interferometry

Heterodyne detection involves mixing waves at two different frequencies and measuring the resulting beat frequency or phase, a process somewhat related to the aforementioned synthetic wave generation. One of the waves is typically referred to as the signal wave and the other the local oscillator. A very small signal wave can cause significant beats in a large local oscillator wave. In a preferred embodiment, the frequency difference between the signal and local oscillator is approximately 80 MHZ. Because a synthetic wavelength is used, there may be two signal and two local oscillator waves. The frequency difference between one signal wave and its corresponding local oscillator wave may be 77.5 MHZ while the frequency difference between a second signal and its local oscillator may be 82.5 MHZ. Frequency differences near 80 MHZ are preferred because efficient acoust-optic frequency shifters are commercially available near this frequency. It is also desirable to keep the difference between the two frequency shifts much larger than the average frequency shift. This is because in signal processing the average frequency oscillations are removed from the difference frequency oscillations by bandpass filtering. As stated earlier, the frequency difference between the two signal waves is a large 754 GHz which generates the 400 micron beat pattern.

Mixing and measuring these 4 waves, each at a different frequency separation, is called superheterodyne detection. This type of measurement may be used to accurately count the beats generated by the interferometer. This type of measurement may also be used to measure the phase of the beat waves generated by the interferometer. NOTE: In practice the heterodyne detection is used to measure the phase difference between the beat wave from the reference and the signal channels. As the output signal beam scans over surface 120, a lens may collect some of the backscattered or reflected light. This light may then be mixed with the local oscillator laser beam. As an example, the optical power collected from surface scatter might be $5 \times 10^{-8}$ W. A local oscillator power of $2 \times 10^{-4}$ W can be used. Because of the way that waves mix, the signal light will cause a power oscillation in the combined laser beam of plus and minus $6 \times 10^{-6}$ W. This oscillation is a factor of 750 above the expected noise level of the detector compared with a factor of only 6 for the raw signal. This example illustrates the power of heterodyne techniques to detect signals that would normally be lost in the background noise. The resulting high signal to noise level can now be used for accurate beat measurement. The power in the local oscillator wave may be adjusted so that shot noise (noise caused by the random arrival of photons on the detector) is slightly larger than the detector noise.

Optical Design

Figure 4:
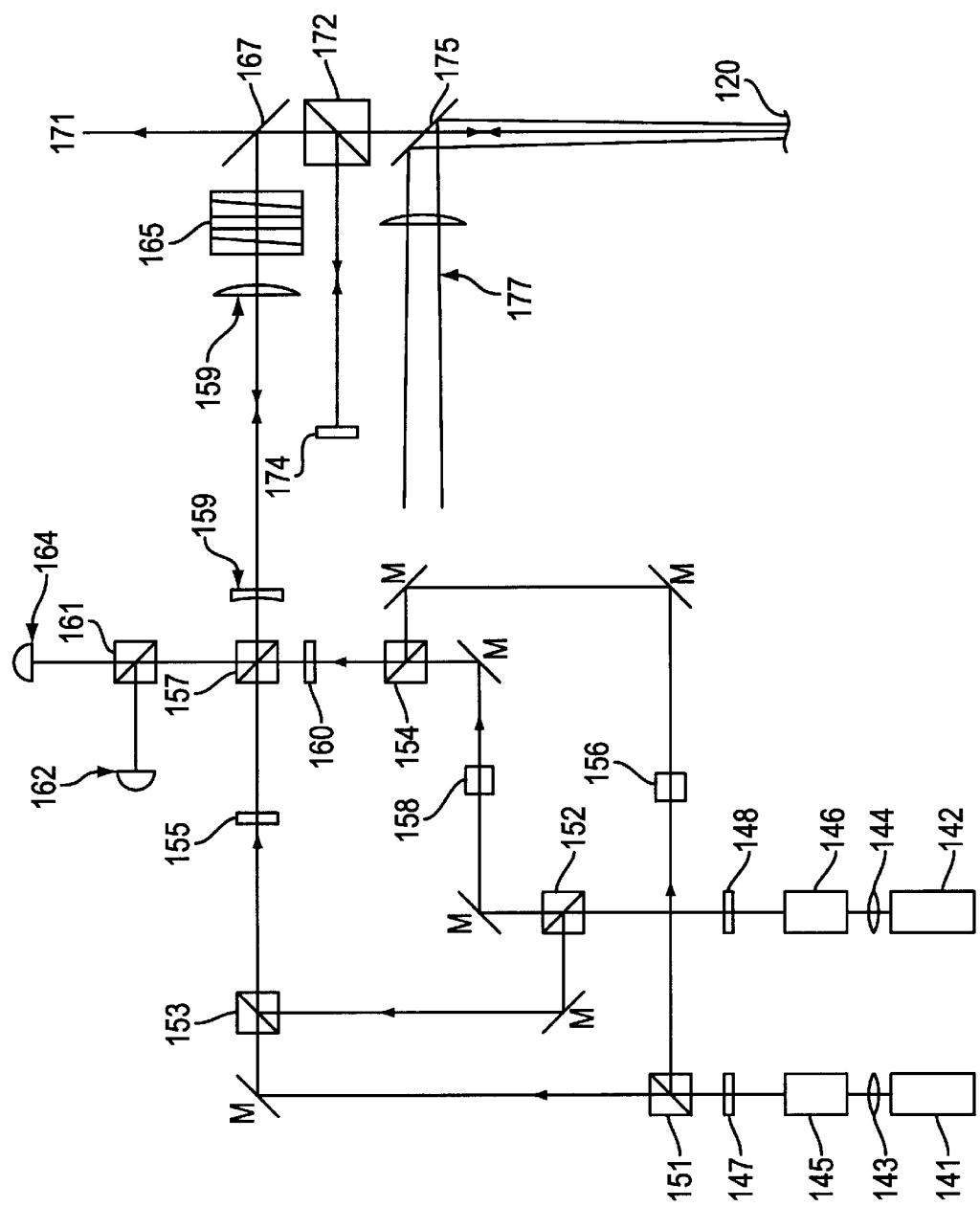
FIG. 4 shows a schematic of the optical paths of the topographer.

FIG. 4 shows an optical diagram of a preferred embodiment of the invention. Two distributed feedback (DFB) diode lasers 141, 142 may generate output beams at 1.5142 microns and 1.5148 microns. Each of these lasers may generate 30 mW of output power with a 1 MHZ linewidth. DFB lasers have been extensively developed over the past few years for use in optical communications and thus make good choices for this application. In addition to having a narrow linewidth, the output from lasers 141, 142 changes very slowly with temperature. Using standard thermoelectric temperature control the output frequency of the lasers can be maintained to approximately 1 part per billion. The tight wavelength tolerance insures that the synthetic wavelength formed by adding the two beams does not change enough to cause problems.

FIG. 4 shows a detailed schematic of the optical path of the topographer, as well as the final portion of the optical path of a corneal ablation system. In addition to the elements described below, FIG. 4 shows a number of mirrors "M". Mirrors M serve no purpose other than to change the direction of a beam so that it is directed to the next optical component in the beam path. The quantity and location of these mirrors will depend on the physical arrangement of the other components, and no particular arrangement of mirrors should be assumed.

Lasers 141 and 142 may generate the two initial laser beams which are used to produce all the other laser beams used in the topographer. The output from the lasers 141, 142 may be collimated by collimators 143, 144 and then passed through Faraday isolators 145, 146, which can prevent light scattered or reflected from optic surfaces from interfering with the frequency stability of the lasers. The outputs from isolators 145, 146 may be polarized at right angles to each other.

Next the beams may pass through wave plates 147, 148, which may be oriented such that a small portion (possibly 10%) of each beam is converted to the opposite polarization, thus making two elliptically polarized beams. The beams may then be split by polarizing beam splitters 151, 152 into their respective 10% and 90% components.

The 90% portions of the two beams may then be combined at polarizing beam splitter 153. This combining is possible because the beams have opposite polarization. After exiting polarizing beam splitter 153, the two linear polarized beam components may be converted to left and right circular polarized beams by quarter wave plate 155. Next nonpolarizing beam splitter 157 can split the beam. Half of the incident light may be sent back through quarter wave plate 155 and eventually blocked by the Faraday isolators 145, 146. The other half of the beam may be sent toward beam expander 159, which can optically expand the width of the laser beam and then focus it, so that the beam will have the desired size when it reaches the target surface. Beam expander 159 is shown as containing two lenses, but the number of lenses may vary.

Next the beam may pass through scanner 165, whose purpose is to scan the beam across the surface of the target in a manner to be described later. The beam may then be reflected by dichroic mirror 167 toward target surface 120. Dichroic mirror 167 may reflect the laser light but transmit visible light, allowing the target surface to be viewed or recorded from position 171. Polarizing beam splitter 172 may divide the beam into linear polarized components. This beam splitter is what finally adds the output from the two diode lasers to form the synthetic wavelength. The s-polarized synthetic wavelength beam can be directed to a reference surface 174, while the p-polarized component can be directed through dichroic mirror 175 to target surface 120. In a corneal ablation system, dichroic mirror 175 can be used to reflect the ultraviolet Excimer laser beam 177 used for performing corneal ablation, while the mirror can be transparent to visible light and the infrared diode laser beam. For other applications, such as machine tool monitoring and vibration measurement, mirror 175 may not be needed.

Backscattered light from both target surface 120 and reference surface 174 may be combined by beam splitter 172, and returned in a reverse direction along the along the same path previously described. At beam splitter 157, a portion of the returned beam may be directed to polarizing beam splitter 161. At polarizing beam splitter 161, the light scattered from target surface 120 may be separated from the light scattered from reference surface 174 because of their opposite polarizations. The light from target surface 120 may be directed to target signal detector 164, while the light from reference surface 174 may be directed to reference signal detector 162.

The interferometer may compare the phase of the beat wave measured by the signal detector 164 with the phase of the beat wave measured by reference detector 162. Because the reference and target beam paths are separated after scanner 165, path changes caused by scanner 165 do not effect the relative number of beats. As previously described for an interferometer, reference surface 174 may be moved parallel to the optical axis to change the detected fringe patterns and number of detected beats.

A Gaussian beam propagation program may be used to calculate the required beam size from beam expander 159 to achieve a spot of desired size at target surface 120. Because a diffraction limited Gaussian laser beam may be used and target surface 120 may be located at the beam focus, speckle effects can be minimized at the detectors.

Referring back to the 10% portion of the laser beams reflected and transmitted by beam splitters 151 and 152, these beams may be frequency shifted by acousto-optic modulators 156 and 158 to generate the local oscillator beams. These two frequency shifts may differ by 5 MHZ in a preferred embodiment. The two frequency shifted beams may be combined by polarizing beam splitter 154 and converted to left and right circular beams by quarter wave plate 160. Half of each component may be transmitted through beam splitter 157. The local oscillator light from both lasers may be mixed at beam splitter 161 to form a second synthetic wavelength. This second synthetic wavelength may be slightly different than the first synthetic wavelength incident on target surface 120 and reference surface 174. The output beams from beam splitter 161 may be directed onto the reference and target detectors 162 and 164, respectively.

Superheterodyne measurement compares the beats in the local oscillator wave with the beats in the signal wave from the target or reference surface. The mathematics of superheterodyne detection are known and are not given here but the method for a preferred embodiment is described. First, the four oscillating components (2 signal and 2 local oscillator) may be added together. All resulting frequency components which are much greater than the approximately 80 MHZ bandwidth of the detector may be discarded. The resulting electrical signal from the detector looks like a beat wave. The high frequency factor can oscillate at the average frequency of the acousto-optic modulators, which is 80 MHZ. The modulation factor can oscillate at half of the 5 MHZ difference frequency. The beat wave electrical signal may be rectified using a full wave bridge and then low pass filtered to generate an oscillating signal at the 5 MHZ modulation frequency. It is the phase of this 5 MHZ signal that is used to analyze beats.

Scanning Pattern

The pattern used for scanning target surface 120 can have a great effect on the quality of the results and on the amount of data that must be processed to achieve those results. For measuring target surfaces with a random or unknown contour, a rectangular grid pattern might be preferred. For surfaces that are contoured in a circular or annular pattern, such as discs, spherical objects, lenses, etc, the preferred pattern can be a spirograph pattern such as pattern 80 illustrated in FIG. 5. Circle 82 defines the outer limits of the scan pattern. In come cases, the scan may extend beyond the area 84 being modified, so that the unmodified outer areas of the scan pattern can provide a reference to determine how much total modification has been completed. This unique scan pattern avoids the huge computational requirements of a full rectangular grid scan, and detects annular irregularities that can be missed with a concentric circle scan. This pattern is especially useful for the corneal ablation application, because it can detect irregularities which can degrade the so-called best-corrected vision by creating defects that cannot be corrected with glasses or contact lenses. This pattern also concentrates the greatest number of data points at the center of the cornea's viewing area, where accuracy is the most critical. Equally important, the pattern can be created by counter-rotating optical wedges, a design that minimizes mechanical vibration by using constant-speed rotation rather than linear acceleration of the optical components.

Referring again to FIG. 4, counter-rotating wedge scanner 165 may include two optical wedges rotating in opposite directions about the optical axis of the beam. In a preferred embodiment, one wedge rotates at 98.2 revolutions per second and the other at 81.8 revolutions per second in the opposite direction, resulting in 180 cross sections per second. High accuracy is obtained because approximately 90 degrees of motor rotation is used to produce one cross section scan over the target surface. This is about 100 times as much motor rotation as required for a single cross-sectional scan in a conventional rotating mirror type scanner. This creates much greater accuracy in the perceived location of each measurement. A further advantage of this configuration is that a 10% increase in motor speed can double the scan density, thus minimizing the torque-induced mechanical effects of rotational acceleration when the scan speed is changed. Since increasing the scan density also increases the time required to make a full scan, this ability to vary the density/speed tradeoff can be used to advantage. Using the slower but more accurate high density scan only at the beginning and end of the operation (whether the operation is corneal ablation, disk machining, or other) can improve the accuracy of the final results while only adding a small percentage to the total operational time.

The spirograph scan pattern generated by the counter rotating wedge scanner is well suited for scanning several cross sections of the cornea. To provide reproducible data it is necessary that the data collection be precisely synchronized with the rotation of the wedges. This synchronization insures that corresponding data collected during subsequent scans actually corresponds to the same place in each scan. It is also possible that only data from certain portions of the scan be collected. For instance, portions of the surface outside area 84 in FIG. 5 might not be modified and therefore might not be of interest. For these reasons, it is desirable that a trigger signal can be generated at the corresponding location in each lobe of the scan pattern.

Figure 8:
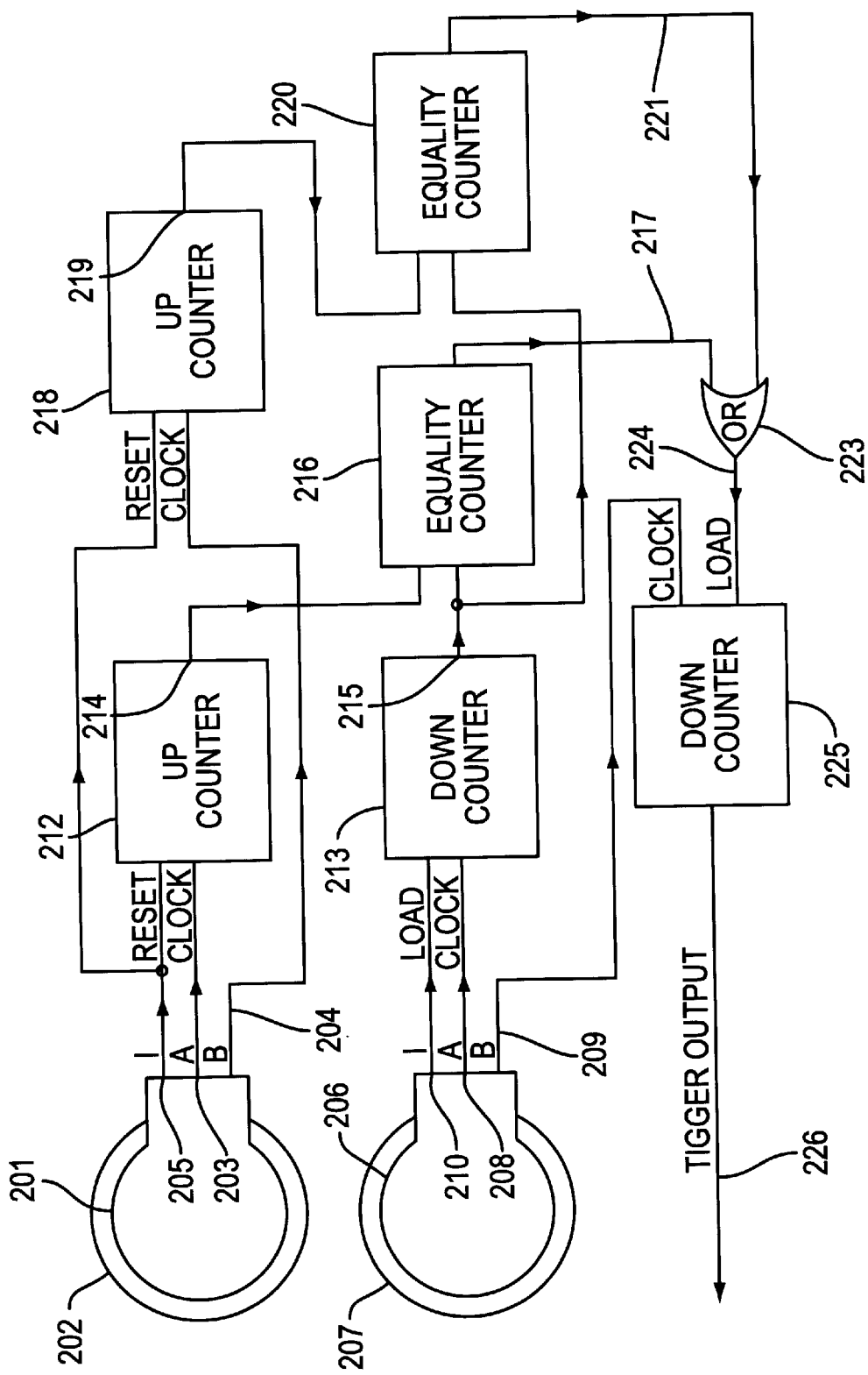
FIG. 8 shows a logic diagram of a signal trigger generator.

A functional circuit for generating the desired trigger signal is shown in FIG. 8. Optical encoders 201, 206 may be attached to the two motors 202, 207 used to drive the wedge scanner. Each encoder may generate output signal A (203, 208), output signal B (204, 209), and index signal I (205, 210). Signals A and B may be digital signals with a selected number of cycles per revolution, and with a 90 degree phase shift between A and B. Index signal I may provide one pulse for each revolution at the same angular location. Signal A from first motor 202 may be used as the clock input to a digital up counter 212, while index signal 205 may be used to reset counter 212. Signal A from the second motor 207 may likewise drive a down counter 213, while index signal 210 may be used to load a preset value into down counter 213, the preset value being equal to the number of pulses delivered by signal A in one revolution of the corresponding wedge. The counter outputs 214, 215 of the up and down counters may be compared with digital equality checker 216, which may produce a pulse at output 217 whenever the count at 214 equals that at 215. Each time the counts at 215 and 216 are equal, the laser beam is at the same location on a lobe of the scan. However, if up and down counters 212 and 213 transition at the same time, their outputs 214 and 215 may never be equal under certain conditions. For example, if the up counter transitions from 236 to 237 at the same time that the down counter transitions from 237 to 236, they will effectively "pass" each other without ever being equal. This problem may be solved by driving a second up counter 218 with signal B (204) which is 90 degrees out of phase with signal A (203). The output count 219 of counter 218 may then be compared with down counter output 215 by a second equality checker 220 to produce a pulse at output 221 when ever the two inputs are equal. Outputs 221 and 217 can then be OR'd so that a pulse from either equality checker 218, 220 can load a preset value into down counter 225. Each pulse from signal B (209) of encoder 206 decrements the count on down counter 225. When the count on down counter 225 reaches a value of zero, an output trigger signal 226 may be generated. Trigger signal 226 can then be used to initiate (or terminate) data collection for each cross section of the spirograph scan pattern.

Optical Fiber Filter

Mixing a portion of the output from two lasers generates the beat waves used for distance measurement. To generate a perfect beat wave, the spatial modes of the two laser beams must be placed exactly on top of each other. When the two beams are placed on top of each other with the same diameter and beam divergence, then a single mode beat wave is generated. If the beams are not placed precisely on top of each other, then different portions of the wave front will have a different phase. Combining two beat waves that are beating at different frequencies generates the superheterodyne signal. If the two beat waves are not properly formed then the phase of the superheterodyne signal will vary over the wave front of the superheterodyne beam.

To form a precisely overlapped beat wave, the output from the two lasers can be overlapped and passed through a length of single mode optical fiber, with a preferred length being approximately one meter. Passing the beams through a length of single mode optical fiber effectively filters the input beams spatially and forces them into the same spatial mode. A polarization-maintaining fiber can be used to maintain the polarization properties of the input beams. If the input beams have opposite polarizations and each beam is coupled into the fiber along one of the fiber's principal axes then the beams will still have opposite polarizations at the output of the fiber.

The use of optical fiber is also beneficial in that the fiber allows the lasers, modulators, and much of the optics to be remotely located from the sensing portion of the interferometer. This can be especially useful in a coordinate-measuring application because it can allow the optical sensor portion of the interferometer to be used as an optical probe for existing coordinate-measuring machines.

Digitization Clock Driven By Reference Channel

Laser frequency fluctuations can cause phase noise in the measured signal in both the reference and probe channels. Vibrations can also cause noise in both channels. Much of the noise caused by these problems can be reduced by removing that portion of the noise that is identical in both the probe and reference channels. Because much of the noise manifests itself as phase variations in the superheterodyne signal, using the reference channel signal to drive the data collection can compensate for some of the noise. Driving the data digitizer with a clock derived from the reference channel can also insure that the number of samples per cycle is fixed. The computational efficiency of calculating the phase of a sampled oscillating signal is much better if the exact number of data points per cycle is known. If the digitizer is driven by a clock that is a multiple of the reference channel oscillation then the number of data points per cycle will be the frequency multiplication factor.

To implement this technique a phase locked loop (PLL) may be used to follow the phase of the reference channel. The PLL may also be used to multiply the frequency of the reference channel signal. The demodulated (rectified and low pass filtered) output from the reference channel can be used for locking. For example, if the demodulated reference signal oscillates a 5 MHZ, the PLL can multiply the frequency by 8 to generate a 40 MHZ clock signal. This clock signal may then be used to drive the digitizer clock input on the analog-to-digital converter that samples both the reference and probe channels. Because the reference surface typically does not have abrupt steps, the signal from the reference channel will not have abrupt phase changes. The absence of abrupt phase changes allows the PLL to remain locked to the phase of the reference signal.

Measurement Speed

Referring back to FIG. 2, two main factors may determine the required measurement speed. First, the topography data needs to be updated fast enough that modification device 22 can respond to any imperfections in the modified shape of target surface 120. Second, the data must be scanned quickly enough to detect or compensate for any motion in target surface 120 that would otherwise introduce errors. Obviously, these factors can vary greatly depending on the particular application.

There are numerous applications that can benefit from a comparatively inexpensive way to measure surface topography within very small tolerances, or alternately to measure the movement of a surface rather than a point. Three of those applications are corneal ablation, precision component machining, and non-contact vibration analysis. Even though they are used in different industries, each can benefit from the topographer of the present invention. Each is described below in more detail.

Corneal Ablation

In recent years it has become possible to perform vision correction by reshaping a patient's cornea through the use of an excimer laser. The excimer laser produces a laser beam with a very short wavelength, typically in the range of 193 nanometers, which can cause biological surface tissue to spontaneously decompose without producing thermal damage to surrounding tissues. Because the radiation is relatively non-penetrating, only the surface layers of tissue are affected. These characteristics have made the excimer laser particularly effective for correcting several types of vision problems by reshaping the contours of the cornea of the eye. By precisely controlling the intensity, direction, beam size, and duration of exposure of the laser beam, the cornea can be reshaped through this process so that it has different refractive qualities. Through proper reshaping, vision defects such as myopia, hyperopia, astigmatism and other vision problems can be corrected, thus reducing or eliminating further need for eyeglasses or contact lenses.

Two basic approaches are currently used in the field. In the first, called photorefractive keratectomy (PRK), tissue is ablated directly from the outer surface of the cornea. This method essentially 'sculpts' the corneal surface directly. In the second approach, called laser-in-situ keratomileusis (LASIK), a thin flexible 'flap' is mechanically sliced off the front of the cornea (except for a small connecting hinge to maintain orientation) and tissue is removed from the newly-exposed inner surface before replacing the flap in its original position. Since the flap is placed onto a surface whose contours have been modified, the resulting contours of the outer surface of the flap are also modified, producing a differently-shaped cornea. Both PRK and LASIK have their respective advantages and disadvantages, but both result in a change in the curvature of the outer surface of the cornea, thus changing the refractive characteristics of the eye. In either case, the amount and location of tissue removal must be precisely controlled to achieve acceptable vision correction.

Unfortunately, both the equipment and the patient introduce a number of variables into this process which may reduce the accuracy of the ablation and therefore degrade the quality of the vision correction. Inaccurate correction can require repetitive treatments, increase the cost, increase the risk of complications, and discourage people from attempting the surgery at all.

Equipment inconsistencies can result from the somewhat variable nature of excimer lasers. The intensity of the energy produced by the laser can vary from one unit to the next, or can vary with time in the same unit, resulting in over- or under-correction. Uneven energy distribution within a cross-section of the laser beam can cause uneven ablation during a single process. These things can affect the amount and distribution of tissue removal and produce unpredictable results.

A number of techniques have been developed to minimize the impact of these variables. Lasers can be frequently recalibrated. Laser beams can be rotated during use to average out irregularities in cross-sectional intensity. Multiple overlapping shallow ablations can be made to average out the irregularities caused by imperfect overlap of narrow beams. Test runs can be made on artificial materials such as polymethylmethacrylate ("PMMA") samples which have a fairly predictable ablation response but do not duplicate the response of biological tissue. A system for accurately measuring ablated PMMA samples is described in international patent application PCT/US98/13539, which is herein incorporated by reference in its entirety. All of these techniques, while helpful, are only indirect attempts to minimize the problems, either by pre-calibrating the laser equipment or by averaging localized errors over a larger area.

Even if the equipment is precisely calibrated, the response of corneal tissue to the laser radiation can vary from patient to patient. Hydration, or the accumulation of moisture, can change the rate at which corneal tissue is ablated by a beam of given intensity. Movement of the eye during the ablation process can redistribute the laser beam over a larger surface area, thus changing the final results. To effectively correct problems such as these, they need to be detected during the surgery so that the ablation can be changed "on the fly". To address this issue, topographers have been developed to measure the cornea's surface during the operation by projecting visible light onto the cornea in a regular pattern such as a grid, and calculating the slope at several points by examining distortion of the reflected pattern caused by the curved surface. This technique, while it addresses the correct problem by measuring realtime results, is generally too inaccurate to give more than general feedback on the amount of correction achieved. Errors that occur between grid lines are undetectable. In addition, this method is generally useful only for measuring light that is reflected rather than scattered. "Reflection" occurs with an optically smooth surface by causing parallel rays to be returned in a predictable parallel direction. "Scattering" occurs with an optically rough surface by causing rays to be returned in multiple random directions. Ablation roughens the ablated surface, causing light to be scattered rather than reflected, thus making reflected-light measurement techniques unreliable.

A completely integrated corneal ablation system utilizing the invention contains two separate but interdependent laser systems—one for ablation of the cornea and one for feedback in the topographer. The actual ablation is preferably performed using an excimer laser or other laser with a wavelength between 180 and 220 nanometers. Very precise pulses of laser energy, typically only nanoseconds in duration, can be directed onto specified portions of the cornea based on a predetermined profile. These pulses cause the surface tissue to ablate, or spontaneously decompose, with the shape of the ablation being dependent on a number of factors, including the fluence of the laser pulses and the number of pulses delivered to each location on the cornea. The precise timing and spatial requirements make it desirable to use a computer to control this operation. Various techniques for performing this ablation process are known in the art and are not repeated here.

In the topographer of the instant invention, measurement of the corneal surface may be performed by using laser radiation that will not adversely affect the eye. Since this radiation should leave the corneal tissues unchanged, the topographer laser beam will preferably be much lower in intensity and with a longer wavelength than that produced by the excimer laser in the ablation device. The topographer laser should be rapidly absorbed in the cornea to prevent scattering from within the cornea from confusing the sensor. A low-power infra-red laser is preferred.

For accurate ablation, the desired amount and location of tissue removal should be known in advance, having been calculated from factors such as the patient's vision characteristics, physical measurements of the patient's eye, and the ablation characteristics of the ablating laser system. The amount and location of radiation which will produce the desired tissue removal can be predicted, based on these factors and the ablation response characteristics of the average cornea. Hence, each ablation will start with a default profile in the form of data which is calculated to produce the desired results. Ablation is usually an incremental process, requiring multiple sequential exposures to radiation ("passes"), and this incremental process can aid greatly in the feedback process. Since incremental results can be measured after each pass, the resulting intermediate corneal shape can be measured by the topographer and compared with the expected shape to detect deviations from the expected contour. This can be accomplished by comparing each incremental result with the final expected contour, but a preferred embodiment compares each incremental result with a predetermined intermediate contour expected for that pass. Succeeding ablation passes can then be modified to accommodate any necessary correction. Through repetitive steps of ablation, topographical measurement, and correction, the ablative process can be repeatedly adjusted to correct for errors as they occur, regardless of the source of such errors. The laser topographer of the present invention is ideal for this application because the surface irregularities of an ablated cornea are within the elevation limits which the invention addresses.

The scan pattern and repetition rate of the measurement can be dictated by the accuracy requirements and reasonable time limits of a corneal ablation operation. In a preferred embodiment, a 15–20 Hz rate for the total scan is preferred, assuming that a typical excimer laser system ablates about 3 microns per second. Patient eye movement is also a concern. For example, if a patient's eye moves while a cross section is being measured then errors will be introduced in the data. Patient-induced transverse movement of the eye is more likely than vertical movement. But due to the slope of the cornea, transverse movement causes less error in the resulting elevation measurement than does vertical movement. In a preferred embodiment, the topographer measures a cross section in less than 4 milliseconds. Each cross section can extend beyond ablation zone 84 so that the unablated portion of the cornea can be used as a reference for both centering and elevation measurements. These reference measurements can be used to remove constant velocity eye movement of the cornea in both vertical and transverse directions. Because the effect of constant velocity movement can be removed, the time allowed for measuring a single cross section is determined by the acceleration of the cornea. Using a 4 millisecond scan time the maximum error seen from such acceleration is typically 1 micron.

Figure 5:
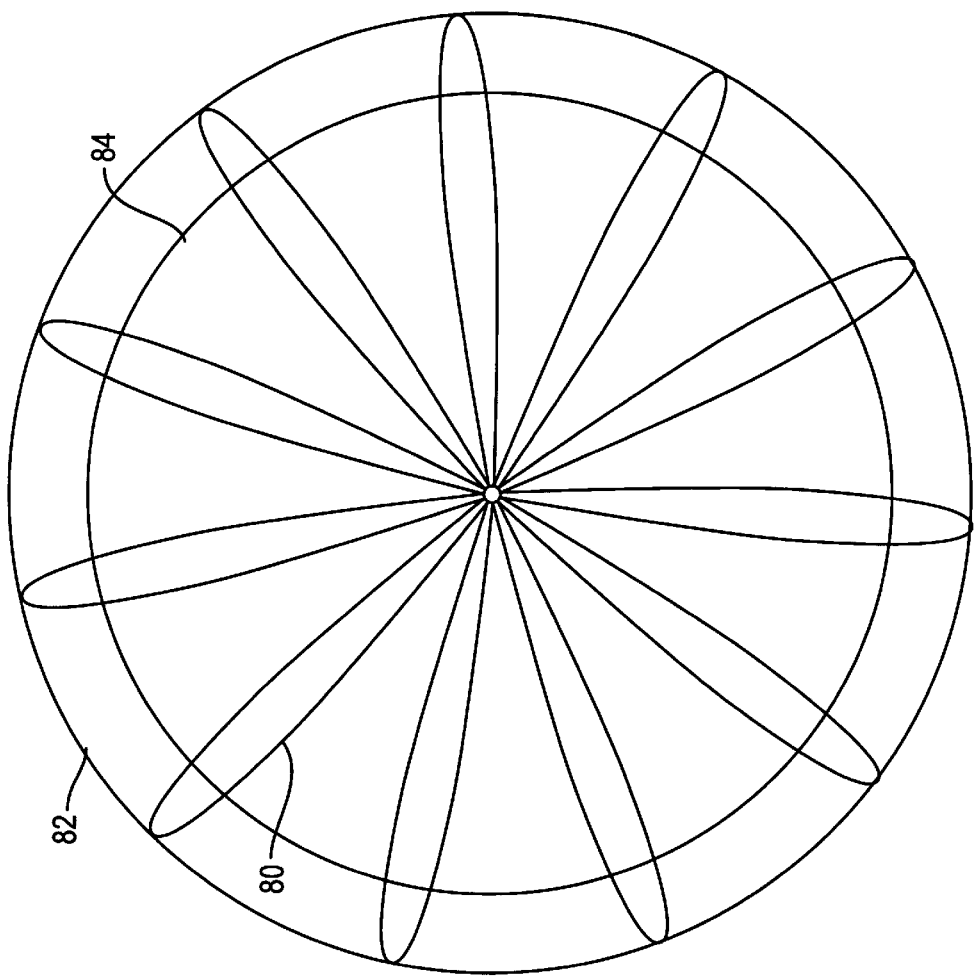
FIG. 5 shows a rotating wedge scan pattern used by the topographer.

In a preferred embodiment, each radial cross section illustrated in FIG. 5 may contain approximately 70 measurement points across a 6 millimeter optical zone, and may be scanned in less than 4 milliseconds with a 50 micron diameter laser beam, while the entire pattern may be scanned approximately 20 times per second. These numbers provide an optimal balance between the considerations of 1) providing sufficient data points for accurate measurement, 2) the speed required for interactive control of the excimer laser during ablation, 3) minimizing error caused by motion of the eye, and 4) keeping the required processing power within feasible limits. While these numbers were considered optimal at the time of the invention, improvements in the cost of computing power and in other areas of technology can bring corresponding improvements in measurement density and speed without changing the basic characteristics of the disclosed topographer.

Multiple Direction Measurement

The spirograph pattern generated by the double wedge counter-rotating scanner can be centered on the apex of the cornea. The interferometer beam can be overlapped with the excimer laser beam using a dichroic beam splitter. This geometry will give the best resolution at the center of the cornea and less accurate resolution as distance increases from the center of the cornea. An alternative embodiment can direct the interferometer beam at the cornea from different directions, preferably using mirrors. This configuration can place multiple spirograph patterns on the cornea at different locations, with the highest resolution for each pattern being located at the center of that pattern. By placing the center of each pattern at a different location on the cornea, multiple high-resolution areas can be created, thus enlarging the area of high resolution. By integrating the data from several directions, a more accurate elevation map of the cornea can be generated. This approach can also be used to avoid the complication of overlapping the interferometer laser beam with the excimer laser beam.

Figure 9:
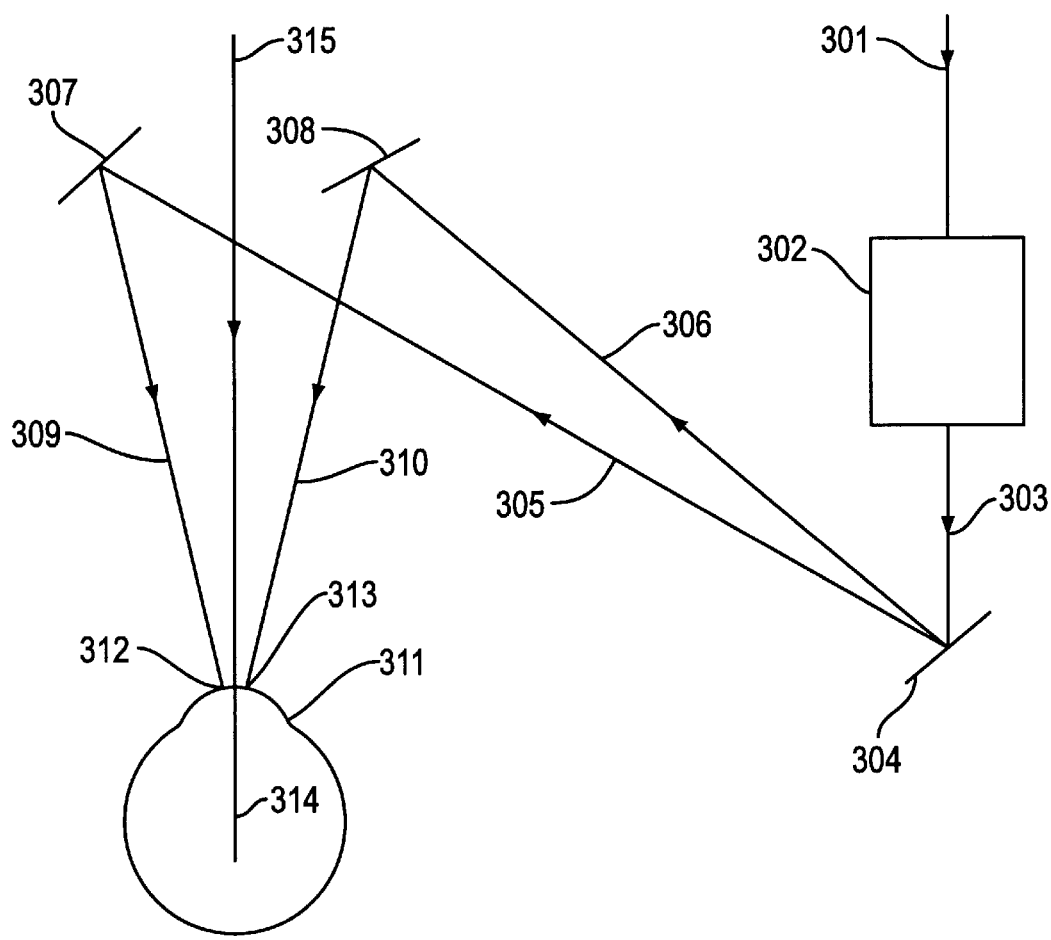
FIG. 9 shows a schematic of an optical path for multiple direction measurement.

As shown in FIG. 9, the synthetic wavelength laser beam 301 may pass through the rotating wedge scanner 302, to produce spirograph pattern beam 303. Beam 303 may then be reflected off a two axis scanning mirror 304, which may direct the reflected beam along multiple possible paths 305, 306 to any of several adjustable mirrors 307, 308. The adjustable mirrors may be positioned to direct the spirograph scan pattern along paths 309, 310 onto cornea 311, with the patterns being centered at 312, 313, away from the cornea's optical center 314. In this configuration, the excimer beam 315 and the topography beams 309, 310 do not overlap, eliminating the need for optical components that can handle both simultaneously. Although FIG. 9 shows two separate optical paths 305/309 and 306/310, any reasonable number of optical paths can be employed, depending on the resolution that is desired and the complexity that can be tolerated.

Angular Tracking for Astigmatism

Correcting for astigmatism requires that the excimer laser ablate in a pattern that is not symmetrical about the optical axis (314 in FIG. 9). For proper results, the astigmatism axis of the eye should be aligned with the astigmatism axis of the laser ablation. However, axis alignment may not always be correct because the patient's eye can rotate in the eye socket. Further degradation may occur because the patient's head cannot be perfectly aligned with the laser system. The orientation of the patient's eye during the pre-operative eye exam can also introduce angular alignment error. As a result of all these factors, conventional systems are unable to achieve consistently accurate alignment of the corneal astigmatism axis and the ablation astigmatism axis.

Due to the spirograph scan pattern used, a topographer of the present invention can accurately measure angular differences in the shape of the cornea, both before and during the ablation process. The astigmatism axis can be tracked because the topographer measures the actual shape of the cornea in real time during the ablation. Thus proper axis alignment can be assured before the ablation begins, and can be corrected during the ablation process if the eye should rotate between scans.

Precision Component Machining

Although conventional manufacturing techniques are suitable for most manufactured products, there are a few products which require manufacturing tolerances within a few microns or even fractions of a micron. An example is a government project to build a new high-energy particle accelerator called the Next Linear Collider (NLC), so called because it will use two beam lines to accelerate electrons and positrons into collision with each other. Acceleration will be generated by microwave power with a wavelength considerably shorter than the wavelengths used in previous linear accelerators. The accelerating structures will be made from approximately 2 million copper disks, each machined to submicron tolerances. It is possible to custom-make a few disks for testing purposes using diamond-turning machines. However, a highly automated manufacturing setup will be required to make this process viable for mass production.

Each disk must be machined from both sides and to the proper thickness. One of the significant problems to be solved is how to mount the disk on the turning machine so that the second surface perfectly matches the first surface. The disks must be very accurately centered on the diamond turning machine so that the second surface features are aligned with the first surface features. In addition, a small burr or spec of dust between the turning machine and disk can cause a non-parallel condition. It is very desirable to have a highly-accurate inspection and feedback system incorporated into the diamond turning machine so that each disk can be machined to the correct dimensions.

The current method of inspecting disks takes several hours per disk and effectively destroys the disk. An optical inspection system is needed to inspect disks in a few minutes without changing or touching the disk surface.

Figure 6:
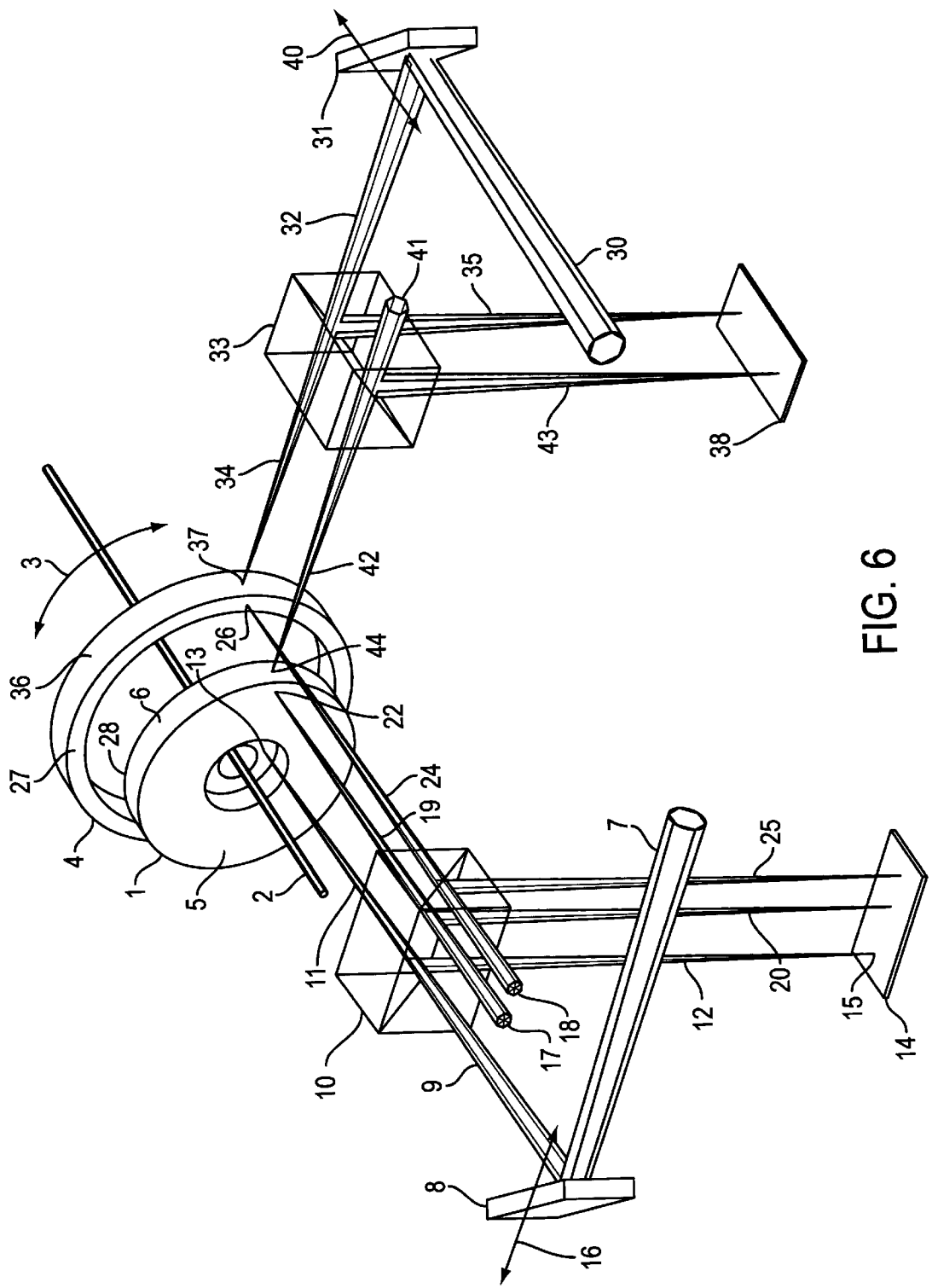
FIG. 6 shows a configuration for machine tool feedback.

FIG. 6 shows an application of the invention for measuring surface tolerances of a disk during a machining operation, and also for determining if the disk and reference ring are properly centered on the machine tool axis. The information gathered from this arrangement can be fed back to the machine tool to improve the accuracy of the operation. The part 1 to be measured may rotate about axis 2 as indicated by arrow 3. Part 1 may be mounted onto the chuck of a lathe or diamond turning machine or any precision spindle. A reference ring 4 with known dimensions can also be mounted on the spindle chuck. Two laser beam setups are shown. One setup is for measuring the front surface 5 of part 1. The second setup is for measuring the outer surface 6 of part 1. The system can be switched from one setup to the other simply by inserting or removing a mirror (not shown) so that the laser radiation travels along either path 7 or path 30.

Laser radiation 7 at a first synthetic wavelength can be incident on mirror 8 and directed along path 9. The laser radiation propagating along path 9 may be divided by beam splitter 10 into a p-polarized component 11 and an s-polarized component 12. The p component 11 can be incident on part 1 at location 13. The s component 12 can be incident on a scattering reference surface 14 at location 15. Mirror 8 may be transversely moved as shown by arrow 16 to change the location at which the laser beam strikes part 1. For example, by translating mirror 8, the laser radiation 7 can be directed along path 17 or path 18. When directed along path 17, the laser radiation may be divided by polarizing beam splitter 10 into p-polarized component 19 and s-polarized component 20. The p-polarized component can contact the face of part 1 at location 22. By moving mirror 8 and rotating part 1, any point on surface 5 can be measured. This measurement compares the distance from beam splitter 10 to surface 5 with the distance from beam splitter 10 to reference surface 14.

When the laser radiation is directed along path 18 and divided into components 24 and 25, the p-polarized component may contact reference ring 4 at location 26 so that the distance to the front surface 27 of the reference ring can be measured. This measurement compares the distance from beam splitter 10 to the reference ring at point 26 with the distance from beam splitter 10 to reference surface 14. Subtracting the distance from beam splitter 10 to surface 5 from the distance from beam splitter 10 to reference surface 27 gives the distance between a point 22 and point 26. If the distance from reference ring 27 to back surface 28 of part 1 is known, then the thickness of part 1 can be determined.

The second setup can measure the circularity and accuracy with which part 1 and reference part 4 are mounted on the spindle. Laser beam 30 at the first synthetic wavelength can be incident on mirror 31 and directed along path 32. This radiation can be divided by beam splitter 33 into a p-polarized component 34 and an s-polarized component 35. The p component 34 can be incident on the outer surface 36 of reference ring 4 at location 37. The s component 35 can be incident on a second reference surface 38. As reference ring 4 rotates about axis 2, the mounting of reference ring 4 on the spindle can be checked. This measurement may give an oscillation at the spindle frequency if reference ring 4 is off center. An encoder (not shown) can be mounted on the spindle to correlate distance measurements with the angular position of the spindle. Mirror 31 can be translated in the direction of arrow 40 to direct laser radiation 30 along path 41. The radiation can be divided by polarizing beam splitter 33 into components 42 and 43, with component 42 contacting outer surface 6 of part 1 at location 44, and component 43 contacting reference surface 38. In the same manner as before, variations in the distance from beam splitter 33 to point 44 can be detected, and can indicate that part 1 is not centered on the spindle. Also, the difference in distance from beam splitter 33 to reference ring surface 36 and from beam splitter 33 to surface 6 can be used to determine the outer diameter of part 1 from the diameter of reference ring 4.

The laser radiation should be focused onto the surface being measured to obtain the best backscatter signal. The range of the focal region (the laser beam confocal parameter) should be adjusted to cover the full range of distances to be measured, including the distance to reference surfaces 14 and 38.

By using the topographer of the present invention, the aforementioned process may be used to determine whether part 1 and reference ring 4 are centered on the turning spindle. Once centeredness has been assured, the process may be used to determine the thickness, diameter, and surface irregularity of part 1 within submicron tolerances.

Vibration Sensor

There are many applications that require measuring surface vibrations. For example, aerospace corporations use vibration-testing facilities to test systems which will fly on aircraft or into space. Such tests can be conducted by physically attaching the test object to a vibrating device, or by using sound waves. Since not every part of the test object will vibrate by the same amount, with the same frequency, or with the same phase, conventional measurements are made by placing accelerometers at several locations. Not only is this process time-consuming, but the mass of the accelerometers can change the vibration characteristics of the test object. A method is needed to quickly and easily measure vibration without physical connection to the test object. The interferometer of the present invention can perform this function by repeatedly mapping the surface contours of the object, and analyzing how various portions of the surface change with time. Each scan can determine the relative elevation of multiple points on that surface. By comparing these elevations with those obtained in successive scans, each point's vibration response can be mapped as the point oscillates up and down. The highest vibration frequency detectable by this method can be determined by the scan rate of the topographer, which is in turn affected by the desired accuracy. Depending on the accuracy required, vibrations up to 100 KHz can be measured in a preferred embodiment. By examining multiple points in each scan, the amplitude, frequency, and phase of vibration at each point can be easily determined from the data, as can cross-correlation data of those factors between the multiple points. An addition benefit is that the measurement device need not physically touch the test object, and thus does not affect it's vibration responses.

Figure 7:
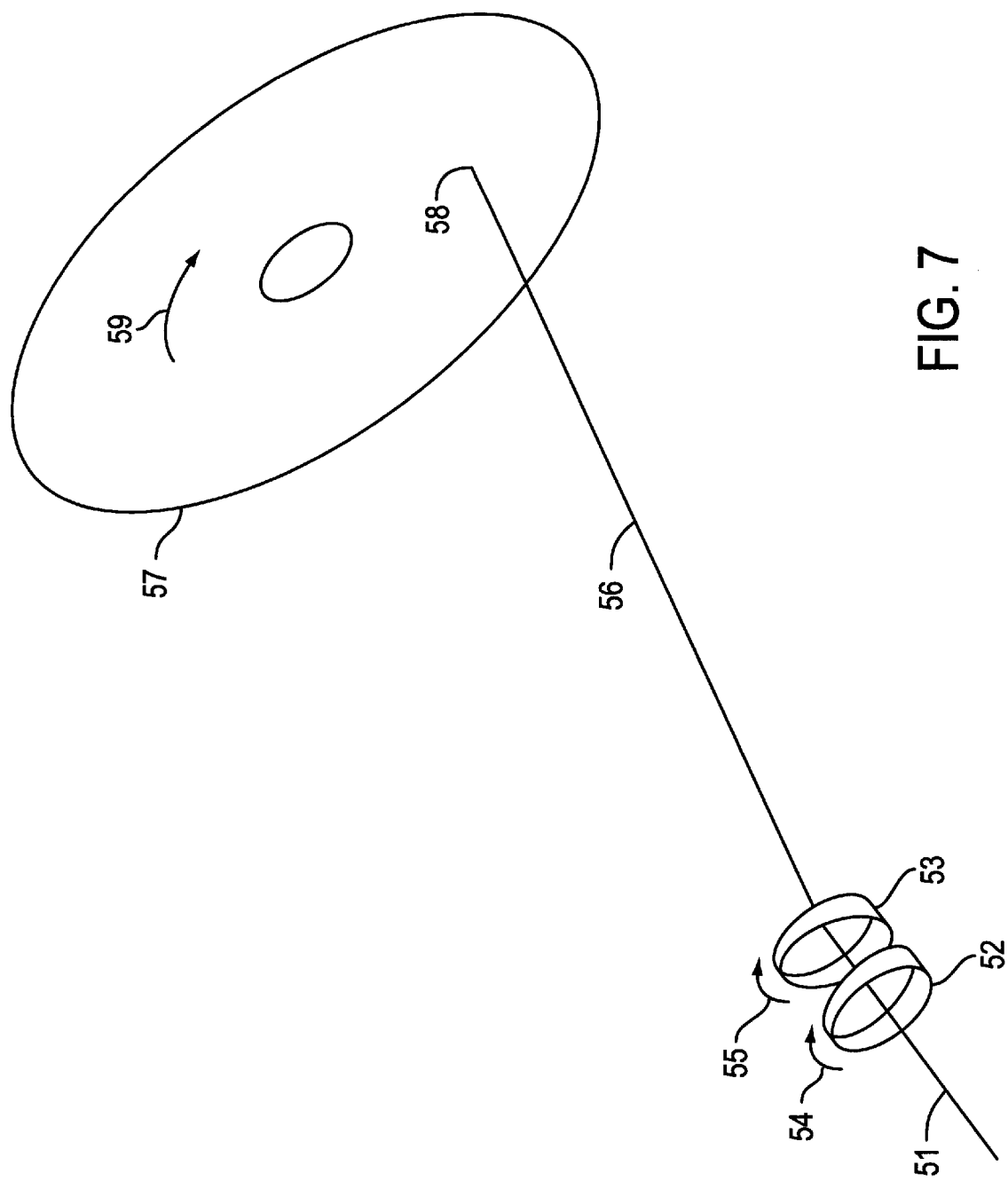
FIG. 7 shows a configuration for generating a circular scan pattern on a rotating object.

FIG. 7 shows how to generate a circular scan pattern. By rotating optical wedges 52 and 53 in the same direction and at the same speed so that they are effectively "locked" together, the laser beam 56 may be deflected from the center axis by a fixed amount, and can trace a circular pattern on target surface 57. If target surface 59 is rotating at the same rate as wedges 52, 53, laser beam 56 will remain on the same point 58 of the target 57 as it rotates. This permits rapid vibration measurements to be taken from the same point on a rotating object. The point being monitored can be changed by momentarily changing the rotational speed of one wedge with respect to the other.

Conversely, rotating target 57 while holding optical wedges 52, 53 stationary (so that point 58 does not move) may permit the topographer to determine if the rotating axis of target 57 is perpendicular to its front surface. A non-aligned rotational axis will be detected by the topographer as a vibration with a frequency equal to the rotational frequency. This may also be used to detect precessional vibration modes in turbines or other spinning objects.

Other Applications

The invention is not limited to the preferred embodiments described above. The topographer can be used to measure the surface contours of many different types of materials. These materials might include biological human or animal tissue, plant biological material, non-biological natural materials such as rocks, minerals, and precious or semi-precious stones, and manufactured products made of natural or man-made materials. The forces used to change the target surface can include radiation, heating, high-speed fluid jets, mechanical removal of material, mechanical addition of material, and mechanical stressing. The methods used to apply these forces can include ablation, evaporation, melting, expansion/contraction, blasting with particles or fluids, sanding, scraping, cutting, machining, bending, and deposition of additional material.

The embodiments described herein are intended to be illustrative and not restrictive. Other variations within the scope and spirit of the invention may occur to those of skill in the art. The scope of the invention is intended to cover all variations to the disclosed embodiments, be defined by the appended claims, and not be limited by the preferred embodiment disclosed.

What is claimed is:

1. A topographer for mapping the surface contours of a target surface, comprising:

a laser radiation generator for producing:
    a first laser radiation with a first wavelength;
    a second laser radiation with a second wavelength;
    a third laser radiation with a third wavelength;
    a fourth laser radiation with a fourth wavelength;
a first synthetic wavelength generator for combining said first and second laser radiations into a fifth laser radiation with a first synthetic wavelength;
a second synthetic wavelength generator for combining said third and fourth laser radiations into a sixth laser radiation with a second synthetic wavelength;
an optical interferometer for mixing the sixth laser radiation with a portion of the fifth laser radiation backscattered or reflected from a target surface and from a reference surface; and
a superheterodyne detector for measuring interference signals from the optical interferometer.

2. The topographer of claim 1, further comprising a polarizing beam splitter for dividing the fifth laser radiation between a target surface and a reference surface.

3. The topographer of claim 1, wherein the laser radiation generator includes a first diode laser for producing the first laser radiation and a second diode laser for producing the second laser radiation.

4. The topographer of claim 1, wherein:
the laser radiation generator includes a first laser and a second laser; and
each of the first and second lasers is frequency stabilized by one of:
distributed feedback;
distributed Brag reflector; and
extended cavity.

5. The topographer of claim 1, wherein:
the laser radiation generator includes a first laser and a second laser; and
each of the first and second lasers is a diode pumped solid state laser.

6. The topographer of claim 1, wherein said first and second synthetic wavelengths are each longer than a vertical step size in the target surface.

7. The topographer of claim 1, further comprising a scanner for controllably directing said fifth laser radiation to said target surface.

8. The topographer of claim 7, wherein said scanner includes first and second rotating optical wedges configured for rotating in one of:
opposite directions; and
the same direction.

9. The topographer of claim 8, wherein said scanner includes first and second rotating optical wedges configured for rotating at one of:
the same angular velocity; and
different angular velocities.

10. The topographer of claim 1, wherein said first and second synthetic wavelengths are each approximately 400 microns.

11. An integrated surface ablation system with feedback, comprising:
a surface contouring system, including data associated with a desired shape of a target surface;
a laser topographer for measuring an actual surface shape of the target surface; and
a feedback system having:
    an input for receiving measured actual surface topography data from said topographer;

a processor for deriving new control data from said measured actual surface topography data;

an output for sending the new control data to said surface contouring system;

wherein said topographer further includes:

a laser radiation generator for producing:

a first laser radiation with a first wavelength;

a second laser radiation with a second wavelength;

a third laser radiation with a third wavelength derived by frequency shifting a portion of the first laser radiation;

a fourth laser radiation with a fourth wavelength derived by frequency shifting a portion of the second laser radiation;

a first synthetic wavelength generator for combining said first and second laser radiations into a fifth laser radiation with a first synthetic wavelength;

a second synthetic wavelength generator for combining said third and fourth laser radiations into a sixth laser radiation with a second synthetic wavelength;

an optical interferometer for mixing the sixth laser radiation with a portion of the fifth laser radiation backscattered or reflected from the target surface and from a reference surface; and a superheterodyne detector for measuring interference signals from the optical interferometer.

12. The system of claim 11, wherein said laser radiation generator includes:

a first laser for producing said first laser radiation; and a second laser for producing said second laser radiation.

13. The system of claim 12, wherein said first and second lasers are frequency stabilized diode lasers.

14. The system of claim 12, wherein said first and second lasers are diode pumped solid state lasers.

15. The system of claim 12, wherein said first and second wavelengths are each between approximately 1 and 2 microns.

16. The system of claim 12, wherein said first and second synthetic wavelengths are each approximately 400 microns.

17. The system of claim 12, further comprising a scanner for controllably directing said fifth laser radiation to the target surface.

18. The system of claim 17, wherein said scanner includes rotating optical wedges.

19. The system of claim 17, further comprising a beam splitter disposed between the scanner and the target surface for directing a portion of the fifth laser radiation onto the reference surface.

20. The system of claim 11, wherein the surface contouring system is a laser ablation system.

21. A system for machining a precision mechanical object, said device comprising:

a programmable machine tool including data associated with a desired shape of a target surface of the mechanical object;

a laser topographer for measuring an actual shape of the target surface; and a feedback system with:

an input for receiving measured topography data from said topographer;

a processor for deriving new control data from said measured topography data;

an output for sending the new control data to the machine tool;

wherein said topographer further includes:

a laser radiation generator for producing:

a first laser radiation with a first wavelength;

a second laser radiation with a second wavelength;

a third laser radiation with a third wavelength derived by frequency shifting a portion of the first laser radiation;

a fourth laser radiation with a fourth wavelength derived by frequency shifting a portion of the second laser radiation;

a first synthetic wavelength generator for combining said first and second laser radiations into a fifth laser radiation with a first synthetic wavelength;

a second synthetic wavelength generator for combining said third and fourth laser radiations into a sixth laser radiation with a second synthetic wavelength;

an optical interferometer for mixing the sixth laser radiation with a portion of the fifth laser radiation backscattered or reflected from the target surface; and a superheterodyne detector for measuring interference signals from the optical interferometer.

22. The system of claim 21, wherein said laser radiation generator includes:

a first laser for producing said first laser radiation; and a second laser for producing said second laser radiation.

23. The system of claim 22, wherein said first and second lasers are frequency stabilized diode lasers.

24. The system of claim 22, wherein said first and second lasers are diode pumped solid state lasers.

25. The system of claim 21, wherein said first and second wavelengths are each between approximately 1 and 2 microns.

26. The system of claim 21, wherein said first and second synthetic wavelengths are each approximately 400 microns.

27. The system of claim 21, further comprising a scanner for controllably directing said fifth laser radiation to the target surface.

28. The system of claim 27, wherein said scanner includes rotating optical wedges.

29. The system of claim 27, further comprising a beam splitter disposed between the scanner and the target surface for directing a portion of the fifth laser radiation onto the reference surface.

30. A vibration testing system for measuring vibrations at a plurality of locations on an object, comprising:

a laser topographer for measuring relative elevations at a plurality of locations of an object;

a sequential control device for initiating said measuring at predetermined time intervals;

an analysis system for comparing sequential measurements for each of the plurality of locations to determine vibration characteristics for each of the plurality of locations; and wherein said topographer includes:

a laser radiation generator for producing:

a first laser radiation with a first wavelength;

a second laser radiation with a second wavelength;

a third laser radiation with a third wavelength derived by frequency shifting a portion of the first laser radiation;

a fourth laser radiation with a fourth wavelength derived by frequency shifting a portion of the second laser radiation;

a first synthetic wavelength generator for combining said first and second laser radiations into a fifth laser radiation with a first synthetic wavelength;

a second synthetic wavelength generator for combining said third and fourth laser radiations into a sixth laser radiation with a second synthetic wavelength;

an optical interferometer for mixing the sixth laser radiation with a portion of the fifth laser radiation backscattered or reflected from said plurality of locations and from a reference surface; and a superheterodyne detector for measuring interference signals from the optical interferometer.

31. The system of claim 30, wherein said laser radiation generator includes:

a first laser for producing said first laser radiation; and a second laser for producing said second laser radiation.

32. The system of claim 31, wherein said first and second lasers are frequency stabilized diode lasers.

33. The system of claim 31, wherein said first and second lasers are diode pumped solid state lasers.

34. The system of claim 30, wherein said first and second wavelengths are each between approximately 1 and 2 microns.

35. The system of claim 30, wherein said first and second synthetic wavelengths are each approximately 400 microns.

36. The system of claim 30, further comprising a scanner for controllably directing said fifth laser radiation to the plurality of locations.

37. The system of claim 36, wherein said scanner includes rotating optical wedges.

38. The system of claim 37, further comprising a beam splitter disposed between the scanner and the plurality of locations for directing a portion of the fifth laser radiation onto the reference surface.

* * * * *